United States Patent [19]

Shah

[11] 4,014,322

[45] Mar. 29, 1977

[54] SPECIMEN COLLECTING DEVICE AND METHOD

[75] Inventor: Nayan S. Shah, Carpentersville, Ill.

[73] Assignee: The Kendall Company, Boston, Mass.

[22] Filed: Oct. 23, 1975

[21] Appl. No.: 625,294

[52] U.S. Cl. .............................. 128/2 F; 23/292; 128/2 W

[51] Int. Cl.² ......................................... A61B 10/00

[58] Field of Search .......... 128/2 F, 2 W, 2 B, 269, 128/275; 193/103.5 R, 127; 23/292

[56] References Cited

UNITED STATES PATENTS

| | | | |
|---|---|---|---|
| 820,004 | 5/1906 | MacMillan | 128/2 F |
| 2,905,169 | 9/1959 | Nieburgs | 128/2 B |
| 3,086,527 | 4/1963 | Forrest | 128/2 W X |
| 3,308,039 | 3/1967 | Nelson | 128/2 W X |
| 3,815,580 | 6/1974 | Oster | 128/2 W |
| 3,890,954 | 6/1975 | Greenspan | 128/2 W |

*Primary Examiner*—Kyle L. Howell
*Attorney, Agent, or Firm*—Powell L. Sprunger

[57] ABSTRACT

A device for collecting aseptic liquid specimens comprising, a container having wall means defining a chamber and an opening communicating with the chamber. The device has liquid sampling means comprising, compressible liquid absorption means for receiving the liquid specimen, and handle means for supporting the absorption means while receiving the specimen and placing the specimen containing absorption means in the chamber through the container opening. The device has means for compressing the absorption means in the container chamber to release the specimen into the chamber.

36 Claims, 10 Drawing Figures

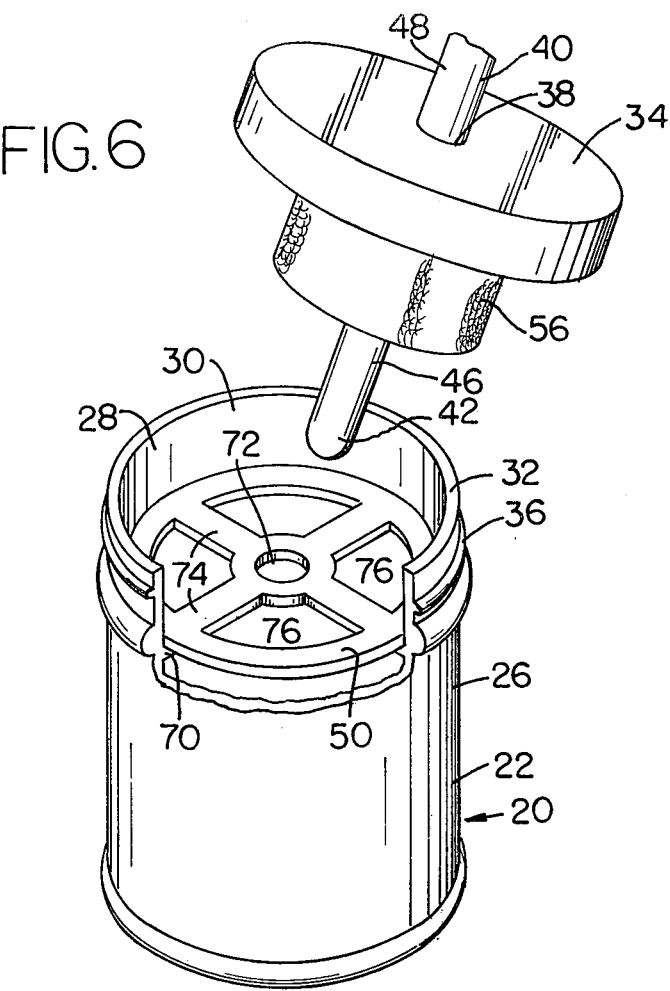
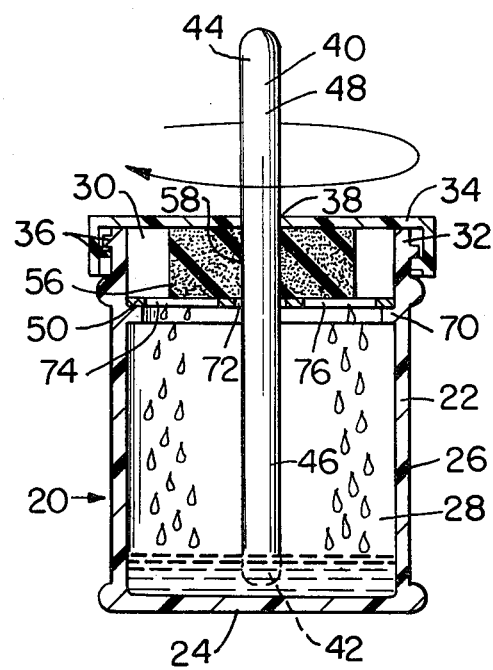
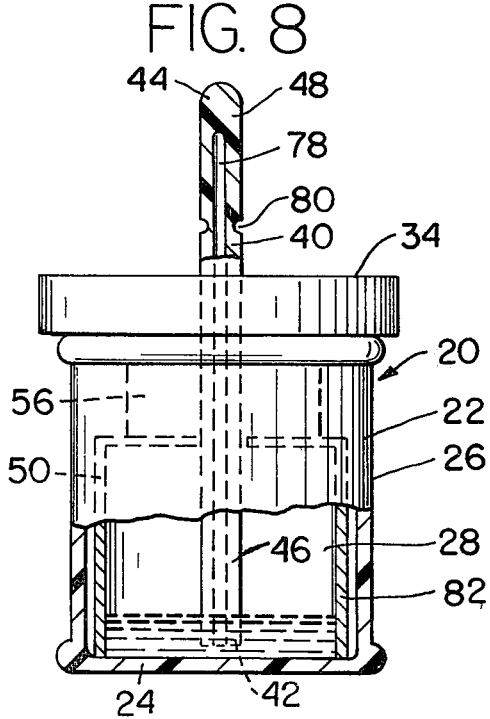
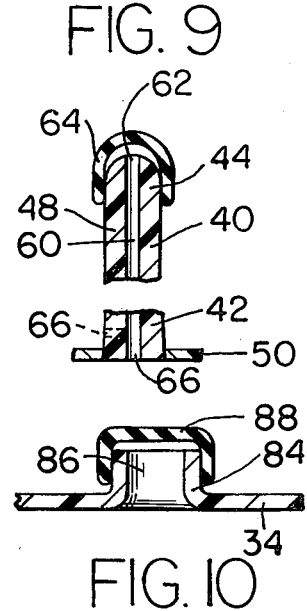

SPECIMEN COLLECTING DEVICE AND METHOD

BACKGROUND OF THE INVENTION

The present invention relates to sampling devices, and more particularly to devices for collecting an aseptic specimen of urine.

Samples of urine must be frequently obtained from patients by physicians for purposes of analysis and possible treatment of the patients. Of course, it is desired that the urine sample be free from contamination to permit proper analysis of the sample. In the past it has been very difficult to consistently obtain an aseptic urine sample from the patient, particularly a female patient, without catheterizing the patient which is an undesirable procedure when solely to obtain the specimen.

It is known that the initial portion of the urine discharge may become contaminated as it passes through the urethra, but a later midstream portion of the discharge is believed relatively free from contamination after the initial portion of the discharge has washed the urethra during voiding. Thus, it is desirable to obtain the urine sample from the midstream portion of the discharge.

Accordingly, patients have been requested to position a container in the urine discharge only after the initial portion of the stream has been voided to capture the midstream portion of the discharge, but this procedure has been unsatisfactory. Initially, patients are reluctant to use the containers in this manner since the discharge splashes about the container and hands as the container is brought into position to receive the midstream discharge, and the physician's aides are equally reluctant to handle the wet container. Additionally, the sample may become contaminated while handling the container and passing it into the urine stream.

SUMMARY OF THE INVENTION

A principal feature of the present invention is the provision of a device for collecting a urine specimen in a simplified and aseptic manner.

The device of the present invention has a container having wall means defining a chamber and an opening communicating with the chamber. The device has liquid sampling means comprising, compressible liquid absorption means for receiving the liquid specimen, and handle means for supporting the absorption means. The device also has means for compressing the absorption means in the container chamber.

A feature of the present invention is that the patient may utilize the handle means for placing the absorption means in the midstream portion of a urine discharge.

Another feature of the present invention is that the absorption means receives and retains the midstream portion of the urine discharge.

Yet another feature of the invention is that the device permits placement of the absorption means in the discharge without splashing of the discharge against the patient's hands.

Still another feature of the invention is that the device permits placement of the absorption means in the discharge without contact of the liquid receiving portion of the device by the hands to prevent contamination of the specimen.

A further feature of the present invention is that the handle means may be utilized to place the absorption means containing the specimen into the container without contact of the absorption means and sample by the hands.

A feature of the present invention is that the compressing means releases the specimen from the absorption means into the container chamber.

Another feature of the present invention is that the specimen is released into the container chamber without contamination of the specimen.

Yet another feature of the invention is that the container may be stored for subsequent analysis of the aseptic specimen.

Another feature of the present invention is the provision of means for removing the handle means from the container for compact storage of the container.

A further feature of the invention is the provision of means for removing the specimen from the container in an aseptic manner for analysis.

Still another feature of the invention is the provision of a method for collecting an aseptic specimen from the urine discharge.

Further features will become more fully apparent in the following description of the embodiment of this invention and from the appended claims.

DESCRIPTION OF THE DRAWINGS

In the drawings:

FIG. 6 is a fragmentary perspective view, partly broken away, showing another embodiment of the specimen collecting device of the present invention;

FIG. 7 is an elevational view, taken partly in section, showing a sponge in the device being compressed to release the specimen into a container;

FIG. 8 is an elevational view, taken partly in section and partly broken away, showing another embodiment of the device of the present invention;

FIG. 9 is a fragmentary sectional view of a shaft for the device of the present invention; and FIG. 10 is a fragmentary sectional view of a sampling port for a lid in the device of the present invention.

DESCRIPTION OF THE PREFERRED EMBODIMENTS

Figure 1:
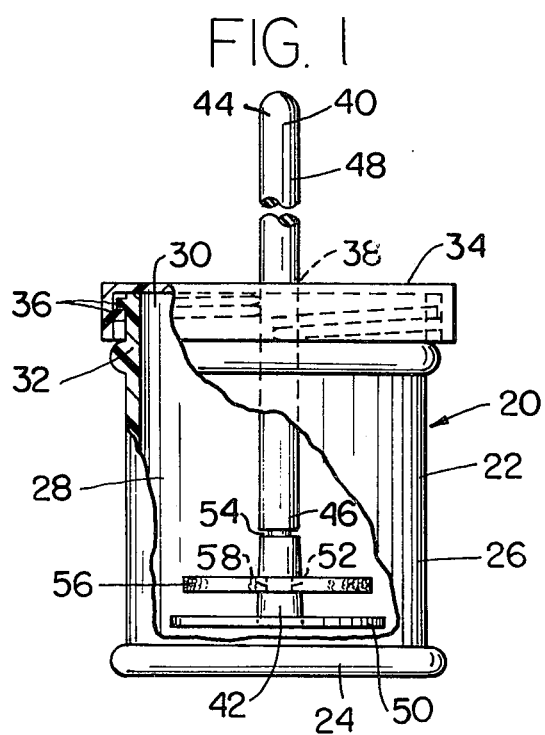
FIG. 1 is a fragmentary elevational view, partly broken away, of a specimen collecting device of the present invention.
Figure 2:
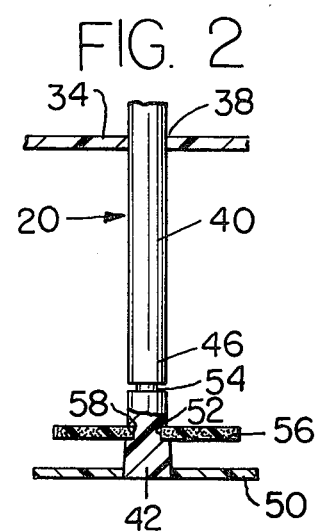
FIG. 2 is a fragmentary elevational view, taken partly in section of the device of FIG. 1.
Figure 3:
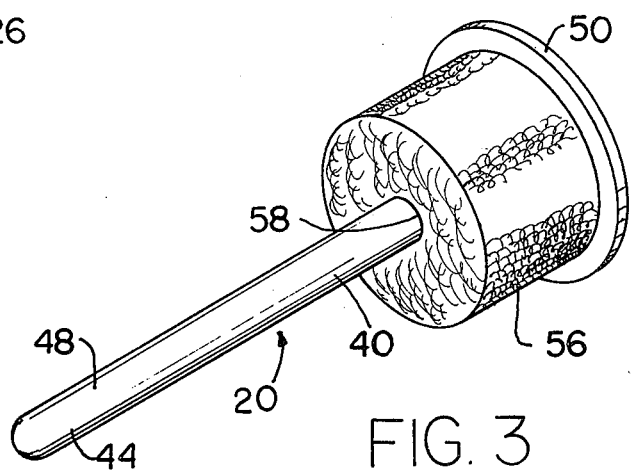
FIG. 3 is a perspective view of a specimen receiving part of the device of FIG. 1.

Referring now to FIGS. 1–3, there is shown a sterile device generally designated 20 for collecting an aseptic sample or specimen of urine. The device 20 has a container 22 having a bottom 24 and a sidewall 26 defining a sterile chamber 28, and having an opening 30 at a top 32 of the container communicating with the chamber 28. The device has a lid 34 releasably attached to the top 32 of the container 22 by cooperating threads 36, such that the lid 34 covers the container opening 30 and closes the chamber 28 when the lid is secured to the container.

The lid 34 has an aperture 38 extending through the lid to slidably receive an elongated shaft 40. When the lid 34 is secured to the container 22, the shaft 40 has an inner end 42 located in the container chamber 28, and an outer end 44 located outside the container, such that an inner portion 46 of the shaft 40 is positioned in the chamber 28 and an outer portion 48 defining a handle for the device is located outside the lid 34.

The device has a circular compression plate 50 attached to the shaft 40 adjacent its inner end 42, such that the plate 50 extends outwardly from the shaft 40. The shaft 40 has a first slot 52 extendng peripherally around the shaft 40 at a location slightly spaced from the plate 50 toward the outer end 44 of the shaft 40. In a preferred form, the width of the slot 52 is approximately equal to or slightly greater than the thickness of the lid 34 for a purpose which will be described below. The shaft 40 also has a second slot 54 extending peripherally around the shaft 40 and spaced slightly from the first slot 52 toward the outer end 44 of the shaft 40. The width of the second slot 54 is less than the thickness of the lid 34 adjacent the aperture 38.

The device has a sterile absorption member or sponge 56 retained on the shaft intermediate the plate 50 and the lid 34. The sponge 56 may be made from a compressed cellulosic material, such as a cellulose sponge sold under the name Normandy by American Sponge and Chamois Company, Inc. of Long Island City, New York. In a preferred form, the sponge 56 may have a generally cylindrical shape defining a generally centrally located bore 58 extending through the sponge 56. Before wetting, the diameter of the bore 58 is preferably of a size less than the outside diameter of the shaft 40 adjacent the slot 52, while the thickness of the sponge 56 is preferably of a size approximately equal to the width of the slot 52, such that the unwetted sponge 56 is retained in position on the shaft 40 in the slot 52. When wetted, the sponge 56 expands both laterally and longitudinally relative the shaft 40, such that lateral expansion of the sponge 56 enlarges the bore 58 to a diameter size greater than the outside diameter of the shaft 40, thus permitting expansion of the sponge 56 longitudinally along the shaft 40, as shown in FIG. 3. In a suitable example, the sponge 56 may have a thickness or length of approximately ⅛ inch (.32 cm.) before wetting, and an enlarged or expanded length approximately equal to 1 inch (2.54 cm.) when wetted. Such a sponge may contain up to twenty cubic centimeters of liquid when saturated.

Before use of the device, the shaft 40 is positioned in the lid 34 at a first inner position with the sponge 56 spaced beneath the lid and exposed for collecting the specimen, as shown in FIG. 1. In a preferred form, the plate 50 may be located adjacent the bottom 24 of the container 22, and the sponge 56 is located slightly above the plate 50. Also, in this configuration, the outer portion 48 of the shaft 40 extends a sufficient distance from the lid 34 to define a handle which may be grasped by the patient's hand. The lid 34 may be removed from the container 22 while the sample receiving part of the device is held by the handle or outer portion 48 of the shaft 40. After the patient has voided an initial part of the urine stream, in the case of a female patient while the cleansed labia is held open, the patient passes the sponge 56 into the midstream portion of the urine discharge while holding the shaft with the handle 48. The sponge 56 absorbs a sample from the midstream portion of the urine discharge while laterally and longitudinally expanding relative the shaft, as previously described. The plate 50, which is located adjacent the sponge 56, prevents splashing of the discharge against the patient during collection of the sample. After a relatively short period of time, such as five to ten seconds, the sponge 56 will have reached its enlarged configuration containing the specimen, as shown in FIG. 3, and the plate 50 and wetted sponge 56 may be inserted into the container chamber 28 through use of the handle, after which the lid may be secured to the container to close the chamber 28. Thus, the midstream portion of the urine discharge may be collected by the sponge 56 without the hands contacting the inner portion 46 of the shaft 40, the sponge 56, or the plate 50 in order to prevent contamination of the sample. Also, the sample is collected by the patient without splashing or wetting the hands, nor is the outside of the container 22 wetted by the discharge during the procedure.

Figure 4:
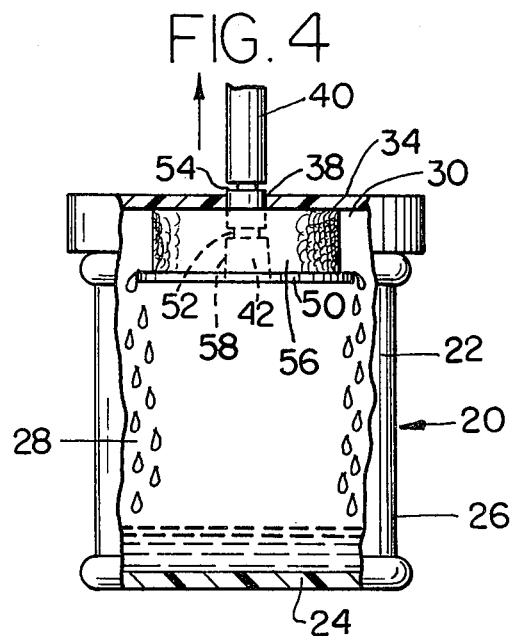
FIG. 4 is a fragmentary elevational view, partly broken away, of the device of FIG. 1 showing the specimen being released from a sponge in the device.
Figure 5:
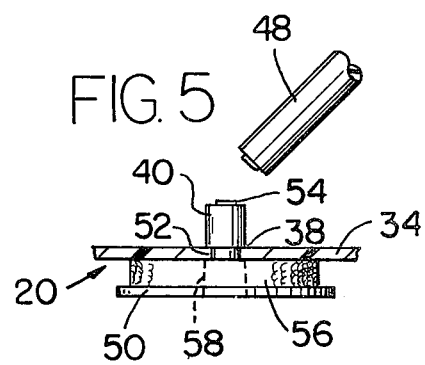
FIG. 5 is a fragmentary elevational view, taken partly in section, showing a handle being removed from the device.

With reference to FIG. 4, after the lid 34 has been secured to the container 22, the shaft 40 may be moved outwardly through the lid aperture 38 to reduce the spacing between the plate and lid, such that the wetted sponge 56 is compressed between the plate 50 and the lid 34 to release the sample in an aseptic manner into a lower part of the container chamber 28. Referring to FIG. 5, as the shaft 40 moves through the lid, the relatively small second slot 54 passes through the lid aperture 38, after which the first slot 52 receives the lid 34 and stops movement of the shaft at a second outer position of the shaft when the specimen has been substantially compressed from the sponge 56. The interengaged lid 34 and slot 52 subsequently retain the sponge in its compressed configuration intermediate the plate 50 and lid 34. As shown in FIG. 5, the handle 48 may be broken from the remainder of the shaft 40 at the second slot 54 which defines an area of weakness in the shaft 40. At this time, the aseptic sample has been collected in the lower part of the container chamber 28, and the handle 48 of the device has been removed to permit compact storage of the chamber and retained sample until ready for analsis when the lid 34 may be removed from the container 22 to pour the aseptic sample from the container.

Another embodiment of a shaft for the device of FIG. 1 is shown in FIG. 9, in which like reference numerals designate like parts. In this embodiment, the shaft 40 has a channel 60 of capillary dimensions extending through the shaft 40. An outer end of the channel communicates with the outside of the shaft 40 through an opening 62 which is covered by a cap 64 releasable attached to the outer end 44 of the shaft 40. An inner end of the channel 60 communicates with the container chamber through an opening 66 at the inner end 42 of the shaft 40, or, as shown in dotted lines, at a location slightly spaced from the compression plate 50 toward the shaft end 44. With reference to FIGS. 5 and 9, when the lid has been received in the first slot 52 of the shaft 40, the sample may be obtained from the container in the following manner. The cap 64 may be removed from the outer end 44 of the shaft 40, and the container may be inverted to a position with the outer end portion 48 of the shaft 40 located below the lid, such that the sample collects above the lid in the chamber and drains through the opening 66, the channel 60, and the opening 62 where it may be received for analysis.

Another embodiment of the device of the present invention is illustrated in FIGS. 6 and 7, in which like reference numerals designate like parts. In this embodiment, the device 20 has a sponge 56 retained on a shaft 40 by suitable means, such as by a slot in the shaft. The shaft 40 is secured to the lid at a fixed position such that the shaft 40 extends through the lid aperture 38 to define a handle 48 and an inner end portion 46. As shown, the container sidewall 26 has a ledge 70 extending peripherally around the inside of the container 22 in the chamber 28. The compression plate 50 extends laterally across the inside of the container and is supported by the ledge 70 at a position in the upper part of the chamber spaced from the lid 34 when the lid is secured to the container 22, with the distance between the retained plate 50 and the attached lid 34 being considerably less than the length of the wetted sponge 56 on the shaft 40. The plate 50 has an aperture 72 aligned with the shaft 40 to receive the inner end 42 of the shaft 40 when the lid 34 is secured to the top 32 of the container 22. Also, the plate 50 has a plurality of radial ribs 74 defining a plurality of openings 76 extending through the plate 50.

After the midstream urine sample has been absorbed in the sponge 56, the inner end 42 of the shaft 40 may be positioned in the plate aperture, and the lid may be moved toward the top 32 of the container 22 and secured in place on the container. During this time, the wetted sponge 56 is compressed between the plate 50 and the lid 34 to release the aseptic sample from the sponge 56. The sample passes from the sponge through the openings 76 to a lower part of the chamber 28 for collection. If desired, the lid 34 may be removed from the container 22, and the sample may be poured from the container for analysis.

Another embodiment of the device 20 of the present invention is illustrated in FIG. 8, in which like reference numerals designate like parts. In this embodiment, the shaft 40 has a channel 78 extending from the inner end 42 of the shaft 40 to a location spaced from the outer end 44 of the shaft 40 in order to define a closed outer end of the shaft, as shown. The shaft 40 has a peripheral slot 80 outside the lid defining an area of weakness adjacent the channel 78. When it is desired to remove the sample from the container chamber 28, an outer section of the shaft 40 may be broken at the slot 80 to expose the channel 78, after which a pipet may be passed through the remaining portion of the channel 78 to the lower part of the chamber in order to withdraw a sample with the pipet. Of course, a shaft 40 of the type shown in FIG. 9 may be utilized for a similar purpose by making the size of the channel 60 sufficiently large to receive the pipet; the cap 64 may be removed from the outer end 44 of the shaft 40 to permit placement of the pipet in the shaft channel 60. Referring again to FIG. 8, the plate 50 may have a depending base 82 to support the plate 50 at a position spaced from the bottom 24 of the container 22.

With reference to FIG. 10, the lid 34 may have an outwardly directed tubular extension 84 defining a port 86, and a cap 88 removably secured to the extension 84. When it is desired to obtain the sample from the container chamber, the cap 88 may be removed from the extension 84, and a pipet may be passed through the port 86 to withdraw the sample from the lower part of the container chamber.

According to a method of the invention, a sterile compressible absorbent member is positioned in a urine discharge to absorb a portion of the discharge. The absorbent member is then compressed by a sterile surface positioned to release an aseptic sample from the absorbent member into the sterile chamber of the container.

The foregoing detailed description is given for clearness of understanding only, and no unnecessary limitations should be understood therefrom, as modifications will be obvious to those skilled in the art.

I claim:

1. A device for collecting aseptic liquid specimens, comprising:
   a container having wall means defining a chamber and an opening communicating with the chamber;
   liquid sampling means comprising, compressible liquid absorption means for receiving the liquid specimen, and handle means for supporting the absorption means while receiving the specimen and placing the specimen containing absorption means in said chamber through the container opening; and
   means for compressing the absorption means in the container chamber after receipt of the specimen to release the specimen into the chamber, said compressing means comprising spaced plate means being movable toward each other with the absorption means supported by the handle means between the plate means to squeeze the absorption means and release the specimen.

2. The device of claim 1 wherein said absorption means comprises a sponge.

3. The device of claim 2 wherein said sponge is made from a compressed cellulosic material.

4. The device of claim 1 wherein said container has a generally cylindrical sidewall surrounding said chamber and defining said opening at a top of the container.

5. The device of claim 1 in which the sampling means includes a lid supported by the handle means.

6. The device of claim 5 including means for releasably securing said lid to the container with the lid covering the container opening.

7. The device of claim 1 wherein the compressing means comprises a pair of first and second spaced plates, with at least one of said plates being movable toward the other plate to reduce the spacing between the plates with the absorption means being located intermediate the plates to compress the absorption means and release the specimen into the chamber.

8. The device of claim 7 wherein said first plate comprises a lid supported by the handle means.

9. The device of claim 8 wherein said handle means comprises a shaft slidably received through an aperture in said lid, said second plate is secured to an inner portion of said shaft, and said absorption means is supported by said shaft intermediate said second plate and lid, whereby said shaft may be moved through the aperture to compress the absorption means between said second plate and lid.

10. The device of claim 8 wherein the sampling means includes a shaft extending from an inner surface of said lid with the absorption means supported on said supported on said shaft, and including means for supporting the second plate in the chamber at a location spaced a distance from the container opening less than the length of said absorption means when containing the specimen, whereby the absorption means is compressed between the lid and second plate when the lid is placed on the container to release the specimen.

11. The device of claim 10 wherein the second plate includes aperture means to receive an inner end of the shaft.

12. The device of claim 10 wherein said second plate includes opening means to permit passage of the specimen through the second plate to a lower part of the chamber.

13. The device of claim 1 wherein the sampling means includes a lid, and in which the handle means comprises a shaft extending through an aperture in the lid, with the absorption means being supported on an inner portion of the shaft relative the lid, and with an outer portion of the shaft defining a handle.

14. The device of claim 13 wherein said shaft has a channel extending from an inner end of the shaft into the outer portion of the shaft with an outer end of the shaft being closed, said outer shaft portion having an area of weakness adjacent the channel to permit breaking of the outer shaft portion and expose the channel, whereby the specimen may be removed from the chamber through the shaft channel.

15. The device of claim 13 wherein said shaft has a channel extending between inner and outer ends of the shaft, and including a cap releasably attached to the outer end of the shaft and covering an outer end of the channel, whereby the cap may be removed to obtain the specimen from the chamber through the shaft channel.

16. The device of claim 1 including a lid, said lid having opening means extending through the lid, and including a cap releasably attached to the lid over the opening means, whereby the cap may be removed from the lid to permit removal of the specimen from the chamber through the opening means.

17. A device for collecting an aseptic specimen from a urine discharge, comprising:
a container having wall means defining a chamber and an opening communicating with the chamber;
a lid having an aperture extending through the lid;
means for releasably securing said lid to the container with the lid covering the opening;
an elongated shaft slidably received in the lid aperture and having inner and outer ends relative said chamber when the lid is secured to the container;
a compression plate secured to and extending outwardly from the shaft;
an absorbent sponge supported on the shaft intermediate said plate and lid, said shaft being movable between a first inner position with the plate spaced from the lid and the sponge exposed beneath the lid to receive a part of the discharge, and a second outer position with the plate located sufficiently near the lid to compress the sponge between the plate and lid and release the specimen into the container chamber.

18. The device of claim 17 wherein said shaft includes an area of weakness positioned adjacent an outer surface of the lid when the shaft is located at said second position, whereby an outer section of the shaft may be broken from the shaft in said area to permit compact storage of the container with the specimen located in the chamber.

19. The device of claim 18 wherein the weakness area comprises a slot extending around the periphery of the shaft, said slot having a smaller width than the thickness of the lid to permit movement of the shaft slot through the lid.

20. The device of claim 17 wherein the sponge has a bore extending through the sponge to receive the shaft.

21. The device of claim 20 wherein said sponge comprises an expansible material which expands from a reduced to an enlarged configuration longitudinally along the shaft when wetted by the discharge.

22. The device of claim 21 including means for retaining the sponge of reduced configuration adjacent said plate prior to wetting of the sponge.

23. The device of claim 22 wherein said sponge is expansible in a radial direction from the shaft when wetted, in which said bore has a diameter of a size less than the outside diameter of the shaft before wetting of the sponge and of a size at least as large as the outside diameter of the shaft when the sponge is wetted, and in which the retaining means comprises a peripheral slot in the shaft adjacent the plate to receive a central portion of the sponge adjacent the bore before the sponge is wetted, said sponge expanding responsive to wetting to release the sponge from said slot.

24. The device of claim 23 wherein said slot has a width at least as large as the thickness of said lid to receive the lid and stop the shaft at said second position.

25. The device of claim 17 including means for stopping said shaft at said second position.

26. The device of claim 17 wherein the shaft includes a channel of capillary dimensions extending through the shaft and communicating between the chamber and the outside of the container when the shaft is located at said second position, whereby the specimen may be drained through said channel with the shaft at said second position and the container in an inverted position.

27. A device for collecting an aseptic specimen from a urine discharge, comprising:
a container having wall means defining a chamber and an opening communicating with the chamber adjacent a top of the container;
a lid having an aperture extending through the lid;
means for releasably securing said lid to the container adjacent the top with the lid covering the opening;
an elongated shaft slidable received in the lid aperture and having inner and outer ends relative said chamber when the lid is secured to the container, a compression plate secured to and extending outwardly from the shaft adjacent the inner end of the shaft, a first slot extending peripherally around the shaft at a location spaced slightly from said plate toward the outer end of the shaft, with said first slot having a width approximately equal to the thickness of said lid, and said shaft having a second slot extending peripherally around the shaft and spaced slightly from said first slot toward the outer end of the shaft, with said second slot having a width less than the thickness of said lid; and
a generally cylindrical absorbent sponge having a bore extending through the sponge with a diameter of a size less than the outer diameter of the shaft adjacent said first slot before the sponge is wetted, with said sponge being received in said first slot before wetting, said sponge being laterally and longitudinally expansible relative said shaft when wetted to release the sponge from the first slot and expand from the plate longitudinally along the shaft, whereby said shaft may be located at a first inner position with the sponge spaced from the lid to receive part of the discharge while an outer end portion of the shaft is held by the user's hand, the lid may be secured to the container with the wetted sponge located in the chamber, the shaft may be moved outwardly through the lid with the second slot passing through the lid and the first slot receiving the lid to stop outer movement of the shaft at a second outer position after compressing the sponge between the lid and plate to release the specimen into the chamber, and an outer section of the shaft may be broken from the remainder of the shaft at said second slot to permit compact storage of the container and specimen.

28. A device for collecting an aseptic specimen from a urine discharge, comprising:
    a container having wall means defining a chamber and an opening communicating with the chamber;
    a lid;
    means for releasably securing said lid to the container with the lid covering the container opening;
    an elongated shaft extending from the lid into the chamber when the lid is secured to the container;
    an absorbent sponge supported on said shaft and being compressible longitudinally along the shaft from an enlarged longitudinal configuration when wetted;
    a compression plate; and
    means for supporting said plate at a fixed position laterally in the chamber while the lid is being secured to the container and spaced a distance from the secured lid a distance less than the length of the enlarged sponge, whereby said sponge may be positioned in the discharge to receive the specimen, and said lid may be secured to the container to compress the sponge between said plate and lid and release the specimen into said chamber.

29. The device of claim 28 wherein said plate includes aperture means to receive an inner end of said shaft.

30. The device of claim 28 wherein said plate includes opening means extending through the plate to permit passage of the specimen from the sponge into a lower part of the chamber.

31. The device of claim 28 wherein said plate extends substantially across the inside of the chamber.

32. The device of claim 28 wherein the supporting means comprises ledge means extending inwardly from the wall means into the chamber for supporting the plate in said container.

33. The device of claim 28 wherein the shaft extends through said lid and includes a handle portion located outside the lid relative the chamber.

34. The device of claim 28 wherein the supporting means comprises a base depending from the plate for supporting the plate at a spaced position from a bottom of the container in the chamber.

35. A device for collecting an aseptic specimen from a urine discharge, comprising:
    a container having a sterile chamber;
    sterile sponge means of a size for placement in the discharge to absorb a portion of the discharge;
    a lid;
    means for releasably securing the lid to the container with the lid closing the chamber;
    means for supporting the sponge means and lid during placement of the sponge means in the discharge; and
    means for compressing the sponge means on the supporting means with a sterile surface against the lid to release an aseptic sample from the sponge means into the chamber.

36. A method of collecting an aseptic specimen from a urine discharge, comprising the steps of:
    positioning a sterile compressible absorbent member in a midstream portion of the discharge with a handle to absorb a portion of the discharge; and
    compressing the absorbent member by a sterile surface positioned to release an aseptic sample from the absorbent member into a sterile chamber of a container while supported by the handle in the container.

* * * * *